(12) United States Patent
Condos et al.

(10) Patent No.: US 6,964,761 B1
(45) Date of Patent: Nov. 15, 2005

(54) METHOD OF TREATING IDIOPATHIC PULMONARY FIBROSIS WITH AEROSOLIZED IFN-γ

(75) Inventors: Rany Condos, Beechurst, NY (US); William Rom, Rye, NY (US); Gerald Smaldone, Setauket, NY (US)

(73) Assignees: New York University, New York, NY (US); The Research Foundation of the State University of New York, Stony Brook, NY (US)

( * ) Notice: Subject to any disclaimer, the term of this patent is extended or adjusted under 35 U.S.C. 154(b) by 0 days.

(21) Appl. No.: 10/318,352

(22) Filed: Dec. 12, 2002

Related U.S. Application Data

(60) Provisional application No. 60/340,826, filed on Dec. 12, 2001.

(51) Int. Cl.[7] .................. A61K 38/21; A61K 45/00; C07K 17/00
(52) U.S. Cl. .............. 424/85.5; 424/85.4; 530/351
(58) Field of Search .................. 424/85.5, 85.4; 530/351

(56) References Cited

U.S. PATENT DOCUMENTS 5,284,656 A    2/1994  Platz et al.

2001/0043906 A1 *  11/2001  Vlasselaer et al. ............ 424/43

FOREIGN PATENT DOCUMENTS

WO        WO 01/36001        5/2001

OTHER PUBLICATIONS

Gross et al. New England J. Med. 2001, vol. 345(7), pp. 517-525.*
Ziesche et al., 1999, N. Eng. J. Med. 341:1264-1269.
Adjei et al., 1990, Pharm. Res., 7:565-569.
Sjodin, L. et al., 1990, Int'l. J. of Pharm., 63:135-144.
Hubbard et al., 1989, A. of Inter. Med., 3;206-212.
Smith et al., 1989, J. Clin. Invest., 84:1145-1146.
Rany Condos et al, IPF: Definition and Diagnosis, NYU School of Medicine Pulmonary and Critical Care Division Grand Rounds, Apr. 6, 2005.
American Thoracic Society, Idiopathic Pulmonary Fibrosis: Diagnosis and Treatment, Am J Respir Crit Care Med, vol. 161, pp. 646-664, 2000.

* cited by examiner

*Primary Examiner*—Janet Andres
(74) *Attorney, Agent, or Firm*—Klauber & Jackson

(57) ABSTRACT

A method of treating idiophathic pulmonary fibrosis (IPF), comprising administering aerosolized interferon-γ in a therapeutically effective amount to achieve improved or ameliorated symptoms of IPF.

10 Claims, 1 Drawing Sheet

A: Lung outline using Xenon Equilibrium image (volume) for patient receiving IFN-γ.
B: Deposition image of same patient showing Regional deposition including stomach region.

METHOD OF TREATING IDIOPATHIC PULMONARY FIBROSIS WITH AEROSOLIZED IFN-γ

This application claims the benefit of Provisional application Ser. No. 60/340,826, filed Dec. 12, 2001.

GOVERNMENT SUPPORT

The research leading to the present invention was supported in part by research NIH grant R01 HL55791, K07 HL03030, and M01 RR00096. The government may have certain rights in the present invention.

FIELD OF THE INVENTION

This invention relates to the treatment of idiopathic pulmonary fibrosis (IPF) with aerosol administration of interferon-γ (IFN-γ), and methods for determination of aerosol deposition. This invention further relates to the dosing of IFN-γ in the treatment of lung cancer.

BACKGROUND

Pulmonary fibrosis of unknown etiology is known as Idiopathic Pulmonary Fibrosis (IPF). It is of insidious onset with nonproductive cough and dyspnea. The estimated five year survival is 30–50%, with a mean survival from the time of diagnosis of 2–4 years (Am. J. Resp. Crit. Care. Med. (2000) 161:646–664).

The pathology of IPF is multifactorial. Bronchoalveolar lavage shows an increase in PMNs, eosinophils, alveolar macrophages, and lymphocytes, as well as increased levels of cytokines, growth factors, and immune complexes. The common final pathway is fibrosis of lung parenchyma with increasing respiratory insufficiency and eventual respiratory failure.

Corticosteroids and cytotoxic agents have been a mainstay of therapy, with only 10–30% of patients showing an initial transient response, suggesting the need for long-term therapy (Mapel et al. (1996) Chest 110:1058–1067; Raghu et al. (1991) Am. Rev. Respir. Dis. 144:291–296).

Due to the poor prognosis of patients with pulmonary fibrosis, new therapeutic approaches are needed.

BRIEF SUMMARY OF THE INVENTION

In one aspect, the invention features a method of treating idiophathic pulmonary fibrosis (IPF) in a subject suffering from IPF, comprising administering aerosolized interferon-γ in a therapeutically effective amount, wherein the symptoms of IPF are improved or ameliorated. In one embodiment, the improved symptoms of IPF are an increase of at least 10% of predicted forced vital capacity (FVC) relative to values prior to treatment.

In another embodiment, the subject suffering from IPF is unresponsive to treatment with one or more of corticosteroid, cyclophosphamide, and azathioprine. Furthermore, in patients that are minimally responsive to immunosuppressant therapies, wherein there is a modest, but insignificant improvement in pulmonary function tests, it is a further aspect of the invention to combine treatment of these patients with aerosolized interferon-γ while maintaining treatment with one or more other therapeutic regimens, including but not limited to treatment with immunosuppressive or anti-inflammatory agents.

In more specific embodiments, aerosolized interferon-γ is administered in doses ranging from about 250 μg to 750 μg given in a nebulizer three times per week. In another embodiment, a dose of 500 μg given in a nebulizer three times per week is preferred. Lower doses may be given depending on the efficiency of the nebulizer. When it is desired to treat IPF patients with a combination of interferon-γ therapy and other treatment modalities, the aerosolized interferon-γ will be titrated to ensure no undesirable effects are experienced by these patients. Furthermore, when combination therapy is a consideration, the other agents may be delivered by a means in which they are considered to be the most effective. This may include intravenous, intramuscular, subcutaneous, or may be combined with IFN-γ and delivered as an aerosol.

In another aspect, the invention features a method of accurately determining upper respiratory airway deposition of an agent administered by aerosol delivery. In one embodiment of this aspect of the invention, the agent administered via aerosol delivery is interferon-γ. This technology is unique and applies to the delivery of IFN-γ to patients with all types of lung disease.

Other objects and advantages will become apparent from a review of the ensuing detailed description taken in conjunction with the following illustrative drawing.

DETAILED DESCRIPTION

Figure 1:
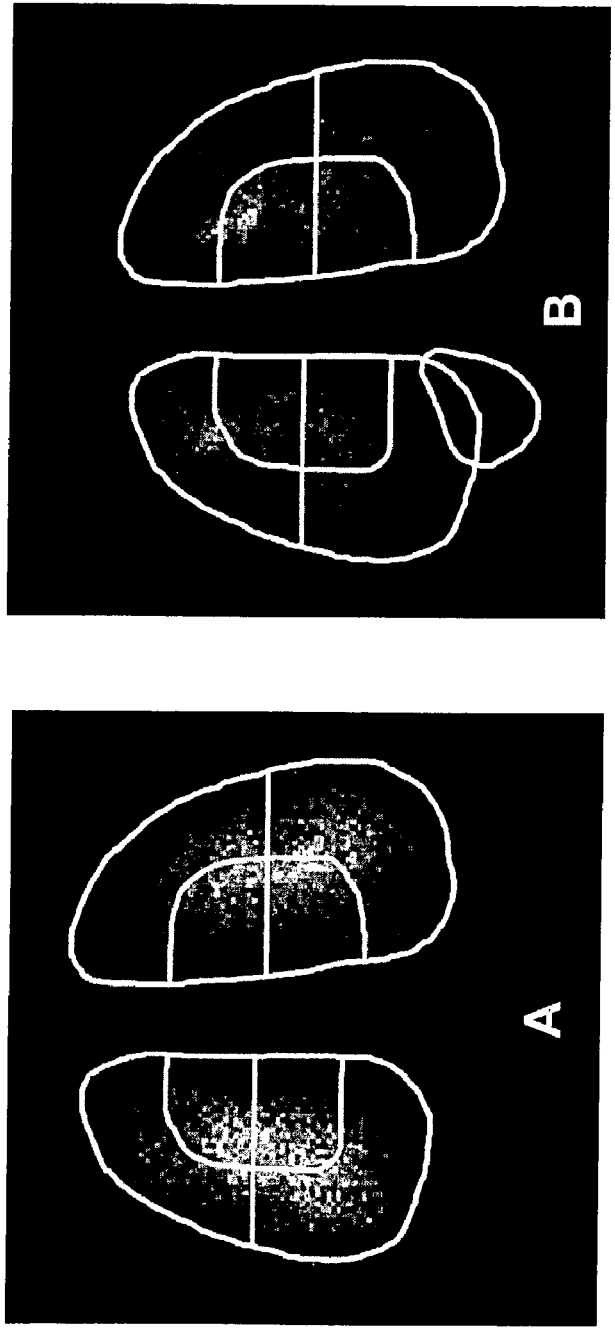
FIG. 1. A deposition scan of a patient suffering with IPF who has been treated three times per week for twelve weeks with 500 μg of IFN-γ delivered via a nebulizer. Imaging was performed following a treatment as described in Example 4. Regions of interest are shown as outlines. sU/L is the distribution of deposited radioactivity in the upper part of the lung to the lower part of the lung normalized for xenon. The horizontal bar in the figure delineates the border between the upper and lower lung quadrants. sC/P means the specific central to peripheral ratio described below. a/Xe means the aerosol to xenon ratio.

Before the present methods and treatment methodology are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms a "an", and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

The term "improved symptoms", in a specific embodiment, is assessed as an improvment of at least 10% of predicted FVC relative to values prior to treatment.

The phrase "unresponsive to treatment with one or more of corticosteroid, cyclophosphamide, and azathioprine" means a patient population that is unresponsive to conventional prior art treatments of IPF.

Vital capacity (VC) means the total air that can be moved in and out of the lungs.

Fev1 means the forced expiratory volume of air in one second.

Fev1/FVC ratio means the ratio between forced expiratory volume in one second and forced vital capacity.

The term "usual interstitial pneumonitis" is synonymous with idiopathic pulmonary fibrosis.

Aerosolized Interferon-γ Treatment of IPF

Recently, a small randomized trial of patients with IPF were treated with subcutaneous interferon-gamma (IFN-γ) (Ziesche et al. (1999) N. Engl. J. Med. 341:1264–1269). Analysis of transbronchial biopsy specimens obtained prior to and six months into therapy with IFN-γ, demonstrated that abnormal pretreatment increases in the profibrotic cytokines transforming growth factor-β (TGF-β) and connective-tissue growth factor (CTGF) were significantly reduced after treatment with IFN-γ (Ziesche et al. (1999) supra). Patients treated with prednisolone alone had no change in levels of TGF-β and CTGF.

Delivery of Interferon-γ

Aerosol Delivery

In a broad aspect of the invention, a method of treating idiopathic pulmonary fibrosis (IPF) in a subject suffering from IPF, comprising administration of aerosolized interferon-γ in a therapeutically effective amount is disclosed, wherein the symptoms of IPF are improved or ameliorated. The improved symptoms of IPF are an increase of at least 10% of predicted FVC relative to values prior to treatment. In a preferred embodiment, aerosolized IFN-γ may be used for treating subjects suffering from IPF wherein the subjects are unresponsive to treatment with one or more corticosteroid, cyclophosphamide, and azathioprine. Furthermore, the administration of aerosolized IFN-γ is calculated and optimized in patients with pulmonary fibrosis. Such administration may result in improvement in pulmonary function tests in IPF patients.

IFN-γ may be administered by several different routes, including intravenous, intramuscular, subcutaneous, intranasally and via aerosol. However, when treating a pulmonary process alone, delivery of medication directly to the lung avoids exposure to other organ systems. Effective administration of 500 μg IFN-γ via aerosol three times per week for two weeks has been shown by bronchoalveolar lavage (BAL) analysis in normal patients to result in increased levels of IFN-γ post-administration.

It is an object of the present invention to deliver interferon-γ via the pulmonary route of administration. IFN-γ is delivered to the lungs of a mammal while inhaling and traverses across the lung epithelial lining to the blood stream. (Other reports of this include Adjei et al., PHARMACEUTICAL RESEARCH, VOL. 7, No. 6, pp. 565–569 (1990); Adjei et al., *International Journal of Pharmaceutics*, Vol. 63, pp. 135–144 (1990); Braquet et al., *Journal of Cardiovascular Pharmacology*, Vol. 13, suppl. 5, s. 143–146 (1989); Hubbard et al., *Annals of Internal Medicine*, Vol. 111, No. 3, pp. 206–212(1989); Smith et al., *J. Clin. Invest.*, Vol. 84, pp. 1145–1146 (1989); Oswein et al., "*Aerosolization of Proteins*", Proceedings of Symposium on Respiratory Drug Delivery II, Keystone, Colo., March, 1990; and Platz et al., U.S. Pat. No. 5,284,656. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass., MistyNeb, manufactured by Allegiance, McGraw Park, Ill.; Aero-Eclipse, manufactured by Trudell Medical International, Canada.

All such devices require the use of formulations suitable for the dispensing of protein. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, may typically comprise protein dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device may generally comprise a finely divided powder containing the protein suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing protein and may also include a bulking agent, such as lactose, sorbitol, sucrose, or mannitol in amounts which facilitate dispersal of the powder from the device, e.g., 50 to 90% by weight of the formulation. The protein should most advantageously be prepared in particulate form with an average particle size of less than 10 μm (or microns), most preferably 0.5 to 5 μm, for most effective delivery to the distal lung.

Nasal Delivery

Nasal delivery of the protein is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Dosages

It is understood that as further studies are conducted, information will emerge regarding appropriate dosage levels for treatment of various conditions in various patients, and the ordinary skilled worker, considering the therapeutic context, age and general health of the recipient, will be able to ascertain proper dosing. Generally, for injection or infusion, dosage will be between 250 μg of biologically active protein (calculating the mass of the protein alone, without chemical modification) to 750 μg (based on the same) given three times per week. More preferably, the dosage may be 500 μg given three times per week. The dosing schedule may vary, depending on the circulation half-life of the protein, and the formulation used.

Administration with Other Compounds

It is a further aspect of the present invention that one may administer the present protein (IFN-γ) in conjunction with one or more pharmaceutical compositions used for treating IPF. Also, anti-inflammatory or immunosuppressive agents may be co-administered, eg. cyclophosphamide, azathioprine or corticosteroids. Administration may be simultaneous or may be in serriatim.

It has been shown that after subcutaneous administration of 250 μg IFN-γ for three days, there was no increase in BAL levels of IFN-γ or alteration of alveolar macrophages, while there was upregulation of peripheral blood monocytes (Jaffe et al. (1991) J. Clin. Invest. 88:297–302). In addition, aerosol IFN-γ has been used as adjunctive therapy in patients with pulmonary tuberculosis.

In the studies described below, patients unresponsive to conventional immunosuppressive therapy suffering from IPF were treated with aerosolized IFN-γ.

The invention may be better understood by reference to the following examples, which are intended to be exemplary of the invention and not limiting thereof.

EXAMPLES

The following examples are put forth so as to provide those of ordinary skill in the art with a complete disclosure and description of how to make and use the therapeutic methods of the invention and compounds and pharmaceutical compositions, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Patient Population

Patient Population. Study subjects were patients as suffering from idiopathic pulmonary fibrosis (IPF) as diagnosed by the American Thoracic Society criteria A or B (below). The patient population had failed to respond to or was not a candidate for conventional therapy with corticosteroids, cyclophosphamide, and/or azathioprine. The patient population was treated with aerosolized IFN-γ for twelve weeks.

Diagnostic Criteria: A. In the setting of a surgical biopsy showing UIP, these three conditions must be met:
1. Exclusion of other known causes of interstitial lung disease, such as certain drug toxicities, environmental exposures, and connective tissue diseases.
2. Abnormal pulmonary function studies that include evidence of restriction (reduced vital capacity (VC) often with an increased Fev1/FVC ratio) and/or impaired gas exchange (increased alveolar-arterial gradient for $O_2$ or decreased diffusion capacity for CO).
3. Bibasilar reticular abnormalities with minimal ground glass opacities on HRCT scans.

B. In the absence of a surgical lung biopsy, in an immunocompetent adult, a presumed diagnosis of IPF may be made if:
  I. All three above criteria are met.
  II. A transbronchial lung biopsy (TBBx) or bonchoalveolar lavage (BAL) shows no features to support an alternative diagnosis.
  III. Three of these four minor criteria:
    1. Age>50
    2. Insidious onset of unexplained dyspnea on exertion
    3. Duration of illness>three months
    4. Bibasilar inspiratory crackles.

Improvement is defined as: (1) An increase of 10% of predicted FVC from baseline value compared to FVC obtained prior to steroid therapy. (2) If a patient has a greater than 10% increase in FVC from baseline value and then returns to baseline value despite therapy.

C. Inclusion Criteria: Patients eligible for inclusion into the study are defined as follows:
  (1) Patients diagnosed with IPF based on accepted criteria (see above) within 3 years of screening;
  (2) Age 20–70;
  (3) A failed trial of prednisone with or without cyclophosphamide/azathioprine or patients in whom treatment with steroids or cytotoxic agents are contraindicated;
  (4) Patient taking 0–15 mg prednisone or the equivalent for 28 days prior to study enrollment and willing to remain on the same dose of corticosteroid;
  (5) FVC 50% and 90% of predicted baseline value at screening;
  (6) $PaO_2$>60 mm Hg at rest on room air;
  (7) Patient able to understand and willing to sign a written informed consent and willing to comply with all requirements of the study protocol including
  (8) Patient fits criteria for research bronchsocopy and is willing to undergo procedure;
  (9) Patient able to have medction administered three times per week at GCRC unit at Bellevue Hospital.

D. Exclusion Criteria: Patients ineligible for inclusion in the study are defined as follows: (1) Patient unwilling or unable to undergo research bronchoscopy; (2) Patient with known asthma or severe COPD; (3) Patient requiring oxygen therapy for maintenance of adequate arterial oxygenation; (4) Patient with hypersensitivity to study medication or other component medication; (5) Patient with known severe cardiac disease, severe peripheral vascular disease or seizure disorder which may be exacerbated by study drug administration (contraindications to drug administration as per package insert); (6) Pregnant or lactating females. Females of child-bearing age will be required to have negative pregnancy test and be required to use accepted form of birth control (abstinence for study duration is the preferred method); (7) Evidence of active infection within one week prior to treatment; (8) Any condition, other than IPF, which is likely to result in the death of the patient within one year from study enrollment; (9) Abnormal serum laboratory values including: (a) Liver function above specified limits: total bilirubin>1.5×upper limits of normal; alanine amino transferase>3×upper limit of normal; alkaline phosphatase>3×upper limit of normal; albumin<3.0 at screening; (b) CBC outside specified limits: WBC<2,500/mm3; hematocrit<30 or >59; platelets<100,000/mm3; (c) Creatinine>1.5×upper limits normal at screening; (10) Drugs for therapy for pulmonary fibrosis, excluding corticosteroids, cyclophosphamide, and/or azathioprine, within the previous six weeks; (11) Prior therapy with any class of interferon medication; (12) Investigational therapy for any indication within the last 28 days.

Example 2

Experimental Design and Methods

Initially, ten patients are recruited from the IPF registry to be enrolled in an open label pilot study of aerosolized interferon-γ. The ten patients will fit the inclusion and exclusion criteria. Data collected includes: past medical history including height, weight, and vital signs; personal history of all medications and complete occupational and smoking history, physical exam, EKG, CBC, electrolyte panel, liver enzymes and coagulation profile, CXR, chest CT, PFT, ABG, an pregnancy test in females of child bearing age.

Each patient completes a *Pulmonary Fibrosis Questionnaire* at the beginning of the study which will question extensively the tobacco exposure, environmental exposures, and medication usage throughout the patient lifetime. Each patient will also complete a symptoms questionnaire which ascertains tolerability of IFN-γ and possible side effects.

The patient will undergo baseline bronchoscopy with bronchoalveolar lavage (BAL) to evaluate the levels of certain pro-fibrotic and inflammatory cytokines. The procedure is performed as follows:

Each patient is evaluated for bronchoscopy as per Bellevue Hospital Protocol. Each evaluation includes: Hgb, platelets, BUN/CR, coagulation panel, ABG with PO2 75 mm Hg, EKG, CXR. Contradictions to bronchoscopy include: lack of patient cooperation, recent myocardial infarction, malignant arrythmias, uncorrectable hypoxemia, unstable bronchial asthma, pulmonary hypertension, partial tracheal obstruction or vocal cord paralysis, bleeding diathesis, and uremia. The patient must be NPO at least 8 hours prior to bronchoscopy. An intravenous line will be placed, supplemental oxygen will be administered, and continuous pulse oximetry and blood pressure monitoring will be performed.

The patient is premedicated with 60 mg IM codeine, viscous lidocaine will be applied to the nose and lidocaine gargle and nebulizer (topical anesthetic bronchoscope) will be used. During the procedure, midazolam and/or morphine may be administered to cause sedation and decrease the cough reflex. These medications are routinely used in bronchoscopy. The bronchoscope is passed through the nose and vocal cords, an an endobronchial exam is peformed. BAL is then performed by administering 50 ml aliquots of sterile normal saline, for a total of 300 ml, and applying gentle suction for maximum return of fluid.

BAL fluid is processed as follows: after BAL fluid is obtained from the patient, it is processed in the GCRC core laboratory under standardized protocol used for processing all BAL. BAL fluid is filtered through sterile gauze. A total cell count with differential is performed in a hemocytometer. Cell viability is determined by the Trypan Blue method. Twenty cytocentrifuge slides are prepared from each lobe of BAL fluid and frozen at −70° C. 24 hour supernatants are collected at a concentration of $10^6$ cells/ml for cytokine ELISA assays. The volume of epithelial lining fluid is determined according to the protein method. Following centrifugation, BAL fluid supernatant is concentrated 10×–50× using the AMICON filter method. Cytokine assays are carried out with commercially available kids (R&D Systems, Minneapolis, Minn.). All samples are assayed in triplicate and the amount of cytokine is quantified at the end of the assay by a microtiter plater reader. Transbronchiall bipsy specimens are processed for isolation of fibroblasts as previously described (Raghu et al. (1989) Am. Rev. Resp. Dis. 140:95–100) and analyzed for collagen production using $^3H$ proline incorporation into collagenous proteins. Each patient is monitored for potential side effects of bronchoscopy, including but not limited to: fever, shortness of breath, hemoptysis, and pneumothorax for 4 hours post procedure in the GCRC by the clinical nursing staff. Concomitant medications will be recorded in the patient's medical record.

Each patient will remain on their stable dose of corticosteroids or immunosuppressant. Investigational therapies are not permitted while the patient is on the study. Pre-clinical rat studies have shown that parenteral IFN-γ decreases the concentration of hepatic microsomal cytochrome P-450. This may cause a decreased metabolism of drugs known to utilize this degradation pathway. If a patient is on any medication known to be metabolized by this pathway, appropriate monitoring procedures will be undertaken.

IFN-γ will be administered via hand-held nebulizer three times a week for twelve weeks. Prior to each dose administration, an exam by the administrating physician will be performed. Peak flow measurements will be performed and the best of three efforts recorded as the pre-treatment value. The Aeroeclipse or Aerotech II nebulizer will be prepared in the usual fashion and 500 μg of drug placed in the nebulizer. The treatment will be administered via compressed air (wall unit or portable) while the patient is in a seated position with nose clips and is breathing normally. At the end of the treatment, the patient is again examined by the study physician and observed on the unit for one hour. One hour after medication delivery, a peak flow reading is obtained and recorded. After the first aerosol treatment, each patient is required to remain on the unit for an additional four hours, when an additional lung exam and peak flow measurement is taken. Each patient is monitored during the administration of IFN-γ for side effects, including but not limited to fever, fatigue, GI abnormalities, headache, cough, shortness of breath, wheezing, and laboratory abnormalities (see Appendixes 3 and 4).

Common Toxicity Criteria. Toxicity is graded with "The Common Toxicity Criteria". Dose modifications are made accordingly. For Grade I toxicity, the patient may continue treatment at the discretion of the physician. For Grade II toxicity (confirmed by immediately repeating abnormal laboratory parameters where appropriate) patient dose is held until a return to less than or equal to a Grade I toxicity, at which time the patient may resume treatment. If Grade II or worse toxicity returns, the patient is withdrawn from the study. For any Grade III or IV toxicity, the patient is withdrawn from the study. Abnormal laboratory parameters should be confirmed.

Example 3

Laboratory Analysis

BAL fluid is used for protein determination and assay of IFN-γ using a viral inhibition assay to determine the amount of drug delivered. Concentrated BAL fluid and 24 hour cell culture supernatants are assayed for cytokines IL-1β, IL-4, IL-6, IL-8 and TNF-α by ELISA (R&D, Minneapolis). Cell-free BAL supernatant is used to measure TGF-β activity by ELISA and luciferase reporter assay. Transbronchial biopsy (TBBX) specimens are used to measure TGF-β gene transcription by semi-quantitative RT-PCR. Fibroblasts are obtained from TBBX specimens, and the quantities of collagen I, III, and fibronectin RNA measured by RT-PCR. RNA (10 μg) is obtained from TBBX or cell culture of TBBX, and Northern Blot analysis is performed. Hydroxyproline protein content is measured by spectrophotometry using BAL fluid, BAL supernatants, and TBBX specimens. BAL fluid cell counts are calculated for each patient, in both pre- and post-treatment samples. A blood sample from each patient is obtained for storage.

Example 4

Deposition Study

Each patient was asked to participate in a deposition study (under separate consent) of IFN-γ administered via handheld nebulizer. This deposition study was designed to study aerosolized IFN-γ as follows: The drug was labeled with 99 mTc and administered via aerosol nebulizer. Using the "attenuation technique", the dose of IFN-γ delivered to various regions of the lung was calculated. The initial dose of 500 μg IFN-γ was used, as this dose has previously been shown to be safe. The dose is adjusted according to deposition studies in each individual patient. A follow up bronchoscopy was performed at the end of the therapy, using the protocol described above. BAL was guided by lung deposition images, so that the areas of highest drug deposition was analyzed and compared to areas of lowest delivered drug and pre-aerosol IFN-γ samples. In this way, total dose to each area of the lung can be calculated and determined. Depending on clinical response and BAL data, dose may be adjusted to reflect optimal clinical and deposition parameters. Attempts will be made to sample similar segments pre- and post-treatment, when possible. Each patient has a follow up evaluation at one month post therapy. The results of all procedures, laboratory evaluations, radiological studies, and pulmonary physiology evaluations are documented in the patient's medical record. All study evaluations are conducted at the GCRC of NYU Medical Center.

The Nebulizer

One commercially available breath-actuated nebulizer was used in this study, the AeroEclipse, whose particle generation is dependent on patient breathing through the nebulizer. It produces aerosol only during inspiration.

The Aerosol:

IFN-γ was radiolabeled using $^{99m}$Technetium diethylene triaminepenta-acetic acid ($^{99m}$Tc-DTPA) for both in vitro and in vivo studies. For AeroEclipse, 2 vials (250 mg of IFN-γ) were used to make up a final volume of 2 mL. AeroEclipse was operated using a Pari Master air compressor (PARI Respiratory Equipment, Inc. Monterey, Calif.).

Setup:

The nebulizers were connected to the circuit in the manner of their clinical use. A ten stage, low flow (1.0 L/m) cascade impactor (California measurements, Sierra Madre, Calif.) was connected using a T connector (T connector$_{cascade}$, Hudson Respiratory Care, Temecula, Calif.). An inspiratory filter, that prevented particles from entering the cascade impactor during expiration, was placed between the piston pump and cascade impactor. A second filter (leak filter) was placed in the system to capture the excess particles directed neither to the inspiratory filter nor to the impactor. To assess possible effects of patient ventilation a piston pump (Harvard Apparatus, Millis, Mass.) was used to simulate a patient's breathing effort.

Prior to inhalation the aerosol was studied on the bench under two conditions:

Standing cloud: The cascade impactor sampled the particles directly from the tubing at 1 Lpm without any ventilation generated by the piston pump (pump disconnected from circuit). For the purpose of generation of particles from AeroEclipse, the breath actuation valve was pressed manually for the duration of sampling.

During Ventilation: The Harvard pump was used to generate a sinusoidal flow in the system, analogous to the breathing of a patient. A tidal volume of 750 mL; Respiratory Rate of 20/m and Duty Cycle of 0.5 was used.

Aerodynamic particle distributions were measured as well as deposition on the connecting tubing to the cascade (T connector$_{cascade}$). The ballistic properties of the aerosol were quantified as the activity on the T connector$_{cascade}$ and reported as a percentage of the activity captured in the cascade impactor (% Cascade). This deposition was used in predicting lung deposition.

Xenon Imaging and Attenuation Studies

For all the subjects IFN-γ deposition was studied using the AeroEclipse nebulizer. Xenon imaging and attenuation studies (see below) were performed.

Lung Volume and Outline Studies ($^{133}$Xenon ($^{133}$Xe) Equilibrium Scan)

The patient was seated in front of a posteriorly positioned gamma camera (Picker Dina camera; Northford, Conn.). After taking a room background image for $^{99m}$Technetium ($^{99m}$Tc), the camera was set for $^{133}$Xe. Breathing tidally at functional residual capacity (FRC), the patient inhaled 5–10 mCi of $^{133}$Xe until the count rate became stable ±10% over 15 seconds. A 1.0 min gamma camera image ($^{133}$Xe equilibrium image) was acquired and stored in a computer (Nuclear Mac v1.2/94; Scientific Imaging Inc. Littleton, Colo.) for analysis. This image was used to define the outer margins of the lung.

Aerosol Deposition Studies

After $^{133}$Xe imaging, the camera was switched to $^{99m}$Tc. Then, the patient inhaled radiolabeled aerosolized IFN-γ from the nebulizer. For each device an expiratory filter was present to capture exhaled particles. The nebulizers were run until dry. After final inhalation, the patient drank a glass of water to wash material from the oropharynx to the stomach. Measuring stomach activity assessed upper airway deposition.

Lung Attenuation Studies (Perfusion Scan)

Lung perfusion scanning was done to calculate the attenuation factor of the lungs. Immediately following deposition imaging, 5mCi of $^{99m}$Tc-albumin macroaggregates were injected via a peripheral vein. It was assumed that all the macroaggregates traversed the right side of the heart and distributed in the lung proportionately to regional perfusion. A one-minute image was obtained. Perfusion was calculated as measured activity minus the activity measured on the previous (deposition) image. The lung attenuation factor was measured by dividing the amount of activity measured by the camera by the amount of activity injected. Lung attenuation factor=Activity measured/activity injected.

Stomach Attenuation:

The patient was given bread with a known amount of $^{99m}$Tc applied to it and a gamma camera picture of the stomach was taken after ingestion. Stomach attenuation was calculated by dividing the activity ingested by activity measured by the gamma camera. Stomach attenuation factor=Activity measured/activity ingested.

Quantification of Deposition:

Using the computer, regions of interest were visually drawn around the stored equilibrium $^{133}$Xe equilibrium scan to define the lung outline and encompass the lung volume. Central lung regions were then drawn that outlined the inner one third of the two-dimensional lung area. After the xenon regions were defined, the same regions were placed over the deposition image and stomach activity identified. Then, a "stomach region" was visually drawn outlining the stomach. If there was overlap between the stomach region and the xenon equilibrium region of the left lung, the overlapping region was defined as "stomach on lung" or SOL. For determination of whole lung deposition, radioactivity from the stomach and the stomach on lung regions were excluded.

Lung deposition was measured using the gamma camera by quantifying activity in the lung regions and applying the appropriate attenuation correction. Oropharyngeal depostion was determined by subtracting the lung activity from the total activity on the deposition image. Appropriate corrections were made for stomach attenuation.

Specific Central to Peripheral Ratio (sC/P)

Specific central to peripheral lung activity was defined by dividing the aerosol image by the xenon equilibrium image. This ratio represents the distribution of deposited aerosol normalized for regional lung volume.

$$sC/P \text{ for aerosol deposition}=(C/P \text{ aerosol}/C/P \text{ xenon})$$

If the aerosol behaves perfectly as a gas and follows the $^{133}$Xe distribution, the sC/P ratio should be 1.0. In our experience particles that deposit preferentially in central airways yield sC/P ratios of 2.0 or higher.

Results of Deposition Study

FIGS. 1A and 1B show significant deposition of aerosol throughout the lungs. When normalized for lung volume, there are relatively more particles in central lung regions than peripheral (sC/P ratio=1.618. There is minimal upper airway deposition.

TABLE 1

| sU/L & sC/P calculations for this patient: | | | | |
|---|---|---|---|---|
| % DEPOSITION | | % DEPO/% VOL | | |
| NORMALIZED: | | a/Xe | sU/L | MEAN sU/L |
| LEFT LUNG | WHOLE-SOL | 1.03 | 0.93 | 0.883 |
| | upper | 0.98 | | |
| | lower | 1.06 | | |
| RIGHT LUNG | WHOLE | 0.97 | 0.84 | |
| | upper | 0.88 | | |

TABLE 1-continued

| sU/L & sC/P calculations for this patient: | | | | |
|---|---|---|---|---|
| | lower | 1.05 | | |
| | | a/Xe | sC/P | MEAN sC/P |
| LEFT LUNG | WHOLE-SOL | 1.03 | 1.37 | 1.618 |
| | central | 1.22 | | |
| | peripheral | 0.89 | | |
| RIGHT LUNG | WHOLE | 0.97 | 1.87 | |
| | central | 1.37 | | |
| | peripheral | 0.74 | | |

We claim:

1. A method of treating idiopathic pulmonary fibrosis (IPF) in a subject suffering from IPF, comprising administering aerosolized interferon-γ in a therapeutically effective amount, wherein the symptoms of IPF are improved or ameliorated.

2. The method of claim 1, wherein the improved symptoms of IPF are an increase of at least 10% of predicted FVC relative to values prior to treatment.

3. The method of claim 1, wherein the subject suffering from IPF is unresponsive to treatment with one or more of corticosteroid, cyclophosphamide, and azathioprine.

4. The method of claim 1, wherein aerosolized interferon-γ is administered at a dose ranging from about 250 to 750 μg three times per week.

5. The method of claim 4, wherein aerosolized interferon-γ is administered as a 500 μg dose three times per week.

6. The method of claim 1, wherein the amount of aerosolized interferon-γ administered is calculated and optimized in patients with idiopathic pulmonary fibrosis.

7. The method of claim 1, wherein said administering results in deposition of interferon gamma in the lungs of patients with IPF.

8. The method of claim 1, wherein said administering results in improvement in pulmonary function tests.

9. A method of treatment of patients having IPF, wherein said method comprises delivery of a therapeutically effective amount of aerosolized interferon gamma plus a therapeutically effective amount of an immunosuppressive or anti-inflammatory agent.

10. The method of claim 9, wherein the immunosuppressive or anti-inflammatory agent is selected from the group consisting of a corticosteroid, azathioprine and cyclophosphamide.

* * * * *